(12) United States Patent
Sanati et al.

(10) Patent No.: US 7,862,601 B2
(45) Date of Patent: Jan. 4, 2011

(54) APPARATUS AND METHODS FOR DELIVERING A STENT INTO AN OSTIUM

(75) Inventors: Arashmidos Sanati, Tehran (IR); Fred Khosravi, Los Altos Hills, CA (US); Jeff Krolik, Campbell, CA (US); Elliot Kim, Santa Clara, CA (US)

(73) Assignee: Incept LLC, Mountain View, CA (US)

( * ) Notice: Subject to any disclaimer, the term of this patent is extended or adjusted under 35 U.S.C. 154(b) by 661 days.

(21) Appl. No.: 11/136,266

(22) Filed: May 23, 2005

(65) Prior Publication Data

US 2006/0265041 A1    Nov. 23, 2006

(51) Int. Cl.
    *A61F 2/06*    (2006.01)
(52) U.S. Cl. .................. 623/1.11; 623/1.15; 623/1.12
(58) Field of Classification Search ............... 623/1.11, 623/1.3, 1.31, 1.15, 1.12, 1.35; 604/103.05, 604/103.06, 103.07, 103.08, 101.01–101.05
    See application file for complete search history.

(56) References Cited

U.S. PATENT DOCUMENTS

| | | | | |
|---|---|---|---|---|
| 4,327,736 | A | * | 5/1982 | Inoue .................. 604/101.05 |
| 4,744,366 | A | * | 5/1988 | Jang .......................... 606/194 |
| 4,763,654 | A | * | 8/1988 | Jang .......................... 606/195 |
| 4,921,483 | A |   | 5/1990 | Wijay et al. |
| 4,950,227 | A |   | 8/1990 | Savin et al. |
| 5,409,495 | A | * | 4/1995 | Osborn ...................... 623/1.11 |
| 5,415,635 | A | * | 5/1995 | Bagaoisan et al. ..... 604/101.05 |
| 5,540,712 | A |   | 7/1996 | Kleshinski et al. |
| 5,545,209 | A | * | 8/1996 | Roberts et al. ............. 623/1.11 |
| 5,549,551 | A | * | 8/1996 | Peacock et al. ........ 604/103.05 |

(Continued)

FOREIGN PATENT DOCUMENTS

EP    0876805 A2    11/1998

(Continued)

OTHER PUBLICATIONS

PCT International Search Report for PCT/US2006/020105, Applicant: INCEPT, LLC, Forms PCT/ISA/220 and PCT/ISA/210, dated Sep. 1, 2006, 5 pages.

(Continued)

*Primary Examiner*—Eduardo C Robert
*Assistant Examiner*—Erin Colello
(74) *Attorney, Agent, or Firm*—William A. English; Vista IP Law Group LLP (57) ABSTRACT

Apparatus and methods are provided for delivering a stent into an ostium. The apparatus includes a catheter including a proximal end, a distal end, and proximal and distal balloons disposed adjacent one another on the distal end. The balloons are expandable independently of one another, and a stent is provided surrounding the balloons. During use, the distal end of the catheter is introduced into a main lumen, and the proximal balloon is inflated to flare a proximal portion of the stent. The distal end is then advanced into the ostium until the flared proximal portion contacts a wall of the main lumen surrounding the ostium. The distal balloon is inflated to expand a distal portion of the stent, e.g., to dilate a lesion within the branch and/or ostium. Thereafter, the balloons are collapsed, and the apparatus is withdrawn, leaving the stent within the ostium.

16 Claims, 7 Drawing Sheets

U.S. PATENT DOCUMENTS

| | | | |
|---|---|---|---|
| 5,607,444 A * | 3/1997 | Lam | 606/194 |
| 5,609,605 A | 3/1997 | Marshall et al. | |
| 5,632,762 A * | 5/1997 | Myler | 606/194 |
| 5,667,486 A | 9/1997 | Mikulich et al. | |
| 5,716,393 A | 2/1998 | Lindenberg et al. | |
| 5,725,535 A * | 3/1998 | Hegde et al. | 606/108 |
| 5,741,333 A | 4/1998 | Frid | |
| 5,749,890 A * | 5/1998 | Shaknovich | 606/198 |
| 5,755,769 A | 5/1998 | Richard et al. | |
| 5,868,777 A * | 2/1999 | Lam | 606/194 |
| 5,902,317 A | 5/1999 | Kleshinski et al. | |
| 6,096,071 A * | 8/2000 | Yadav | 623/1.15 |
| 6,210,429 B1 * | 4/2001 | Vardi et al. | 623/1.11 |
| 6,325,826 B1 * | 12/2001 | Vardi et al. | 623/1.35 |
| 6,409,755 B1 | 6/2002 | Vrba | |
| 6,761,734 B2 * | 7/2004 | Suhr | 623/1.35 |
| 6,821,295 B1 * | 11/2004 | Farrar | 623/1.31 |
| 6,858,038 B2 * | 2/2005 | Heuser | 623/1.35 |
| 7,105,015 B2 * | 9/2006 | Goshgarian | 623/1.11 |
| 2002/0045928 A1 * | 4/2002 | Boekstegers | 623/1.11 |
| 2002/0077691 A1 * | 6/2002 | Nachtigall | 623/1.12 |
| 2002/0091434 A1 * | 7/2002 | Chambers | 623/1.11 |
| 2002/0169498 A1 * | 11/2002 | Kim et al. | 623/1.15 |
| 2002/0183780 A1 * | 12/2002 | Wang | 606/194 |
| 2003/0083734 A1 * | 5/2003 | Friedrich et al. | 623/1.15 |
| 2003/0097169 A1 * | 5/2003 | Brucker et al. | 623/1.11 |
| 2004/0006381 A1 * | 1/2004 | Sequin et al. | 623/1.12 |
| 2004/0015231 A1 * | 1/2004 | Suhr | 623/1.35 |
| 2004/0077987 A1 * | 4/2004 | Rapacki et al. | 604/8 |
| 2004/0093058 A1 * | 5/2004 | Cottone et al. | 623/1.11 |
| 2004/0093061 A1 * | 5/2004 | Acosta et al. | 623/1.11 |
| 2004/0102838 A1 | 5/2004 | Killion | |
| 2004/0106973 A1 * | 6/2004 | Johnson | 623/1.11 |
| 2004/0138731 A1 * | 7/2004 | Johnson | 623/1.11 |
| 2004/0181272 A1 * | 9/2004 | Chambers | 623/1.11 |
| 2004/0254627 A1 * | 12/2004 | Thompson et al. | 623/1.11 |
| 2004/0260378 A1 * | 12/2004 | Goshgarian | 623/1.11 |
| 2005/0049678 A1 * | 3/2005 | Cocks et al. | 623/1.15 |
| 2005/0049680 A1 * | 3/2005 | Fischell et al. | 623/1.15 |
| 2005/0055077 A1 * | 3/2005 | Marco et al. | 623/1.11 |
| 2005/0101968 A1 | 5/2005 | Dadourian | |
| 2005/0149166 A1 * | 7/2005 | Schaeffer et al. | 623/1.13 |
| 2005/0154447 A1 * | 7/2005 | Goshgarian | 623/1.15 |
| 2005/0171597 A1 * | 8/2005 | Boatman et al. | 623/1.22 |
| 2005/0171598 A1 * | 8/2005 | Schaeffer | 623/1.35 |
| 2005/0177221 A1 * | 8/2005 | Mustapha | 623/1.11 |
| 2005/0192656 A1 * | 9/2005 | Eidenschink | 623/1.11 |
| 2005/0209673 A1 * | 9/2005 | Shaked | 623/1.11 |
| 2005/0209674 A1 * | 9/2005 | Kutscher et al. | 623/1.11 |
| 2005/0222668 A1 * | 10/2005 | Schaeffer et al. | 623/1.13 |
| 2005/0288769 A1 | 12/2005 | Globerman | |
| 2006/0041303 A1 * | 2/2006 | Israel | 623/1.11 |
| 2006/0058864 A1 * | 3/2006 | Schaeffer et al. | 623/1.11 |
| 2006/0106455 A1 * | 5/2006 | Furst et al. | 623/1.31 |
| 2006/0135985 A1 * | 6/2006 | Cox et al. | 606/194 |
| 2006/0155356 A1 * | 7/2006 | Israel | 623/1.11 |
| 2006/0224233 A1 | 10/2006 | Grinfeld | |
| 2006/0229700 A1 * | 10/2006 | Acosta et al. | 623/1.11 |
| 2007/0073376 A1 * | 3/2007 | Krolik et al. | 623/1.11 |
| 2007/0078505 A1 * | 4/2007 | Dimitrov | 623/1.11 |
| 2007/0088425 A1 | 4/2007 | Schaeffer | |
| 2007/0173920 A1 * | 7/2007 | Eidenschink | 623/1.11 |
| 2007/0179592 A1 * | 8/2007 | Schaeffer | 623/1.35 |
| 2007/0208408 A1 * | 9/2007 | Weber et al. | 623/1.11 |
| 2007/0219611 A1 * | 9/2007 | Krever et al. | 623/1.11 |
| 2008/0033525 A1 * | 2/2008 | Shaked et al. | 623/1.11 |
| 2008/0208307 A1 * | 8/2008 | Ben-Muvhar et al. | 623/1.11 |
| 2008/0221655 A1 | 9/2008 | Miller | |
| 2008/0243233 A1 | 10/2008 | Ben-Muvhar et al. | |

FOREIGN PATENT DOCUMENTS

| | | | |
|---|---|---|---|
| EP | 1512381 A2 * | 3/2005 | |
| GB | 2385530 A * | 8/2003 | |
| WO | 9717101 A | 5/1997 | |
| WO | WO 9936015 A1 * | 7/1999 | |
| WO | WO 00/44307 * | 8/2000 | |
| WO | 2005041810 | 5/2005 | |
| WO | 2006085304 | 8/2006 | |

OTHER PUBLICATIONS

PCT Written Opinion for PCT/US2006/020105, Applicant: INCEPT, LLC, Forms PCT/ISA/237, dated Sep. 1, 2006, 6 pages.

USPTO, Office Action for US Patent Publication No. 2007/0067011, Mar. 27, 2008, 20 pages.

Office Actions and Responses filed from pending U.S. Appl. No. 11/466,442, dated Mar. 27, 2008 to Feb. 9, 2009, 87 pages.

* cited by examiner

APPARATUS AND METHODS FOR DELIVERING A STENT INTO AN OSTIUM

FIELD OF THE INVENTION

The present invention relates generally to apparatus and methods for delivering an endoluminal prosthesis, e.g., a stent, into a body lumen and, more particularly, to apparatus and methods for delivering a stent into an ostium of a blood vessel or other body lumen.

BACKGROUND

Tubular endoprosthesis or "stents" have been suggested for dilating or otherwise treating stenoses, occlusions, and/or other lesions within a patient's vasculature or other body lumens. For example, a self-expanding stent may be maintained on a catheter in a contracted condition, e.g., by an overlying sheath or other constraint, and delivered into a target location, e.g., a stenosis within a blood vessel or other body lumen. When the stent is positioned at the target location, the constraint may be removed, whereupon the stent may automatically expand to dilate or otherwise line the vessel at the target location. Alternatively, a balloon-expandable stent may be carried on a catheter, e.g., crimped or otherwise secured over a balloon, in a contracted condition. When the stent is positioned at the target location, the balloon may be inflated to expand the stent and dilate the vessel.

Sometimes, a stenosis or other lesion may occur at an ostium or bifurcation, i.e., where a branch vessel extends from a main vessel. For example, such a lesion may form within a coronary artery immediately adjacent the aortic root. U.S. Pat. No. 5,749,890 to Shaknovich discloses a stent delivery assembly for placing a stent in an ostial lesion. U.S. Pat. No. 5,632,762 to Myler discloses a tapered balloon on a catheter for positioning a stent within an ostium. U.S. Pat. No. 5,607,444 to Lam discloses an expandable ostial stent including a tubular body and a deformable flaring portion. Published application US 2002/0077691 to Nachtigall discloses a delivery system that includes a sheath for holding a stent in a compressed state during delivery and a retainer that holds a deployable stop in an undeployed position while the delivery system is advanced to a desired location.

Accordingly, apparatus and methods for delivering a stent within an ostium would be useful.

SUMMARY OF THE INVENTION

The present invention is directed to apparatus and methods for delivering stents or other endoluminal prostheses, and, more particularly, to apparatus and methods for delivering a stent into an ostium or bifurcation of a blood vessel or other body lumen, e.g., for dilating or otherwise lining and/or treating an occlusion or other lesion at the ostium.

In accordance with one embodiment, an apparatus is provided for delivering a prosthesis into an ostium of a body lumen. The apparatus may include an elongate tubular member including a proximal end, and a distal end sized for introduction into a body lumen. A first expandable member may be provided on the distal end of the elongate member, and a second expandable member may be provided on the distal end of the elongate member adjacent the first expandable member, the second expandable member being expandable independently of the first expandable member. The apparatus may include a prosthesis including a first portion surrounding or otherwise adjacent the first expandable member and a second portion surrounding or otherwise adjacent the second expandable member. The second expandable member may be expandable for expanding the second portion to an enlarged condition while the first expandable member and the first portion remain in a contracted condition. The first expandable member may be expanded for expanding the first portion to an enlarged condition that is smaller than the second portion in its enlarged condition.

Optionally, the apparatus may include a constraint, e.g., an overlying sheath for covering at least the first portion, for maintaining the first portion in the contracted condition while the second expandable member is expanded. The constraint may be movable for covering and uncovering the first portion. Optionally, the constraint may also be movable for covering and uncovering the second portion, e.g., independently of the first position.

In one embodiment, the second expandable member may include a transverse surface when expanded that is disposed adjacent the first expandable member, e.g., for deforming the second portion of the prosthesis transversely as the second expandable member is expanded.

In accordance with another embodiment, an apparatus is provided for delivering a prosthesis into an ostium of a body lumen that includes an elongate member including a proximal end, a distal end sized for introduction into a body lumen, a first expandable member on the distal end of the elongate member including a length for receiving a first portion of a tubular prosthesis thereon, and a second expandable member on the distal end of the elongate member adjacent the first expandable member for receiving a second portion of the tubular prosthesis thereon. A portion of the second expandable member may be attached to the first expandable member, while the second expandable member may be expandable independently of the first expandable member for expanding the second portion to an enlarged condition while the first portion remains in a contracted condition.

In addition, the apparatus may include a stent or other prosthesis including a first portion surrounding the first expandable member and a second portion surrounding the second expandable member. In one embodiment, in an enlarged condition, the second expandable member may define a transverse surface adjacent the first expandable member for expanding the second portion of the prosthesis to a flared condition to facilitate placement of the prosthesis within an ostium.

In accordance with another embodiment, a method is provided for implanting a prosthesis within an ostium or bifurcation extending from a main lumen into a branch lumen, e.g., using an elongate member including first and second expandable members on a distal end of the elongate member. Initially, the distal end of the elongate member may be advanced into the main lumen with first and second portions of the prosthesis adjacent the first and second expandable members, respectively. The second expandable member may be expanded to cause the second portion of the prosthesis to expand transversely, and the distal end may be advanced into the ostium until the expanded second portion contacts a wall of the main lumen surrounding the ostium and the first portion of the prosthesis is disposed within the branch lumen. The first expandable member may be expanded to expand the first portion of the prosthesis to contact a wall of the branch lumen.

Thereafter, the first and second expandable members may be collapsed, and the elongate member may be withdrawn from the branch and main lumens, leaving the prosthesis with the first portion expanded within the branch lumen and the second portion contacting the wall of the main lumen surrounding the ostium.

In one embodiment, the first portion may be constrained while the second expandable member is expanded, and the constraint may be removed before expanding the first expandable member. In addition, the second portion may be at least partially deformed as the distal end of the elongate member is advanced into the ostium such that the second portion conforms at least partially to a shape of the wall of the main lumen surrounding the ostium.

In another embodiment, the prosthesis may be provided on the elongate member with the first and/or second portions relaxed in a contracted condition for delivery. As the first and/or second expandable members are expanded, the first and/or second portions may be plastically deformed outwardly, e.g., to dilate or otherwise line the lesion. In still another embodiment, the first and/or second portions of the prosthesis may be biased to expand from a contracted condition for delivery on the elongate member towards an enlarged condition. For example, a constraint may be provided that maintains the first and/or second portions of the prosthesis in the contracted condition. When the constraint is removed, the first and/or second portions may automatically expand towards the enlarged condition. Thereafter, the first and/or second expandable members may be expanded to expand the first and/or second portions further, e.g., to plastically deform or otherwise engage the prosthesis with the ostium, e.g., to dilate an occlusion or other lesion at or adjacent the ostium.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE PREFERRED EMBODIMENTS

Figure 1:
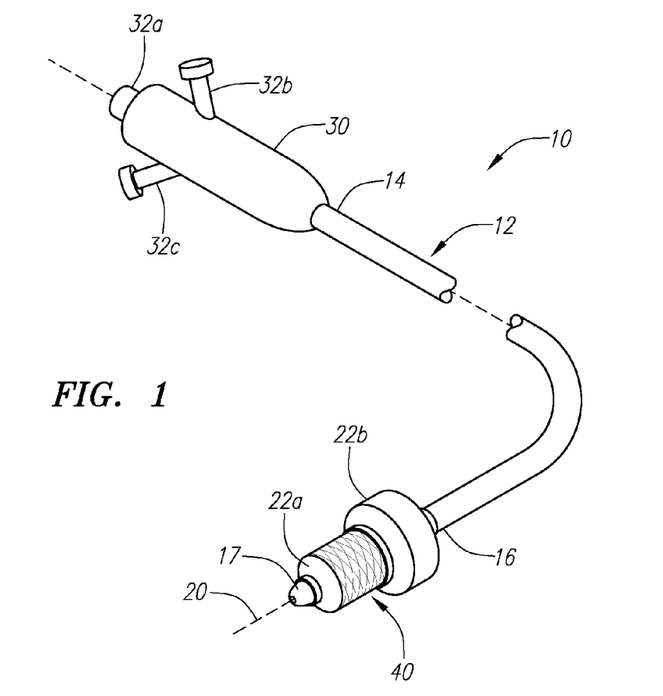
FIG. 1 is a perspective view of an exemplary embodiment of a balloon apparatus for delivering a stent into an ostium.
Figure 2:
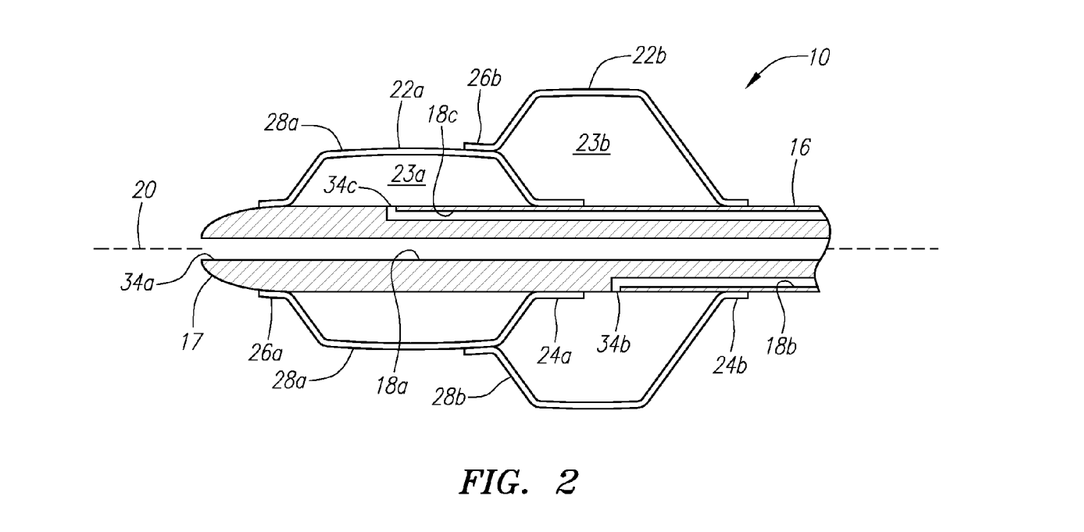
FIG. 2 is a cross-sectional side view of a distal end of the apparatus of FIG. 1.

Turning to the drawings, FIGS. 1 and 2 show an exemplary embodiment of a balloon apparatus 10 for delivering a stent or other prosthesis 40, e.g., into an ostium or other bifurcation between a main lumen and a branch lumen (not shown). Generally, the apparatus 10 includes a catheter or other elongate tubular member 12 having a proximal end 14, a distal end 16, and one or more lumens 18 extending between the proximal and distal ends 14, 16, thereby defining a longitudinal axis 20 between the proximal and distal ends 14, 16. One or more balloons or other expandable members 22 are provided on the distal end 16, e.g., a first distal balloon 22a and a second proximal balloon 22b as shown. Optionally, one or more additional expandable members (not shown) may be provided on the distal end 16 adjacent the first and/or second balloons 22a, 22b.

The catheter 12 may be formed from one or more tubular bodies, e.g., having variable flexibility along its length. For example, the distal end 16 may be substantially flexible to facilitate insertion through tortuous anatomy, e.g., terminating in a rounded or other substantially atraumatic tip 17. The distal end 16 may be sized and/or shaped for introduction into a body lumen, e.g., having a diameter between about one and seven millimeters (1-7 mm), or less than 1.5 mm. The proximal end 14 may be substantially flexible or semi-rigid, e.g., having sufficient column strength to facilitate advancing the distal end 16 through a patient's vasculature by pushing on the proximal end 14. The catheter 12 may be formed from plastic, metal, or composite materials, e.g., a plastic material having a wire, braid, or coil core, which may preventing kinking or buckling of the catheter 12 during advancement.

As shown in FIG. 1, the catheter 12 may include a handle 30 on the proximal end 14, e.g., to facilitate manipulating the apparatus 10. The handle 30 may include one or more side ports 32 communicating with respective lumens 18 within the catheter 12. The handle 30 may be molded, machined, or otherwise formed from plastic, metal, or composite material, e.g., providing an outer casing, which may be contoured or otherwise shaped to ease manipulation. The proximal end 14 of the catheter 12 may be attached to the handle 30, e.g., by bonding, cooperating connectors, interference fit, and the like. Optionally, if the apparatus includes any actuatable components (not shown, see, e.g., FIGS. 6A-6C) on the distal end 16, the handle 30 may include one or more actuators (not shown), such as one or more slides, dials, buttons, and the like, for actuating or otherwise manipulating the components on the distal end 16 from the proximal end 14, as explained further below.

As best seen in FIG. 2, the catheter 12 includes at least three lumens 18 extending between the proximal ends 14, 16. For example, the catheter 12 may include an instrument lumen 18a that extends from a port 32a in the handle 30 to an opening 34a in the distal tip 17. The instrument lumen 18a may have sufficient size to allow a guidewire or other rail or instrument (not shown) to be inserted therethrough, e.g., to facilitate advancing the catheter 12 over the rail, as explained further below. Optionally, the handle 30 may include one or more seals (not shown) adjacent the port 32a, e.g., e.g., a hemostatic seal that prevents fluid, e.g., blood, from flowing proximally out of the port 32a, yet allows one or more instruments to be inserted therethrough and into the instrument lumen 18a.

In addition, the catheter 12 may include inflation lumens 18b, 18c that extend from respective side ports 32b, 32c in the handle 30 through the catheter 12 to openings 34b, 34c on the distal end 16. Each opening 34b, 34c communicates within an interior 23a, 23b of a respective balloon 22a, 22b. The side ports 32b, 32c on the handle 30 may include connectors, e.g., a luer lock connector (not shown), one or more seals (also not shown), and the like. A source of inflation media and/or vacuum, e.g., a syringe filled with saline (not shown), may be connected to the side ports 32b, 32c, e.g., via tubing (also not shown), for expanding and/or collapsing the balloons 22. As shown in FIG. 2, the lumens 18 are disposed adjacent one another. Alternatively, the lumens 18 may be disposed in concentric or other arrangements within the body of the catheter 12. In addition, if the apparatus 10 includes additional balloons (not shown) on the distal end 16, the catheter 12 may include one or more additional inflation lumens (also not shown), and the handle 30 may include one or more additional ports (also not shown), similar to those shown and described with reference to FIG. 2.

Alternatively, other configurations of lumens may be provided for delivering fluid to and/or aspirating fluid from one or both balloons 22. For example, a single lumen may be provided (not shown) that communicates with the interiors 23 of both balloons 22. This embodiment may allow the balloons 22 to be expanded and/or collapsed substantially simultaneously using a single syringe or other source of fluid/vacuum. In another alternative, the catheter 12 may include separate inflation lumens 18b, 18c, but the handle 30 may include a single side port (not shown) to which a syringe or other source of fluid/vacuum may be connected. In this alternative, the handle 30 may include a switch, stopcock, valve, or other device for selectively connecting one or both inflation lumens 18b, 18c to the side port. For example, a three-way valve may be directed to first or second positions to allow the side port to be connected to either of the inflation lumens 18b, 18c, e.g., for inflating/collapsing an individual balloon 22a, 22b. In a third position, the side port may be connected to both lumens 18b, 18c for inflating/collapsing both balloons 22 simultaneously. This configuration may be particularly useful for quickly collapsing both balloons 22 after implanting the stent 40 before removing the apparatus 10. In addition, the configuration may facilitate expanding the entire stent 40, e.g., after expanding and anchoring the first portion 42 and/or after flaring the second portion 44.

Figure 3:
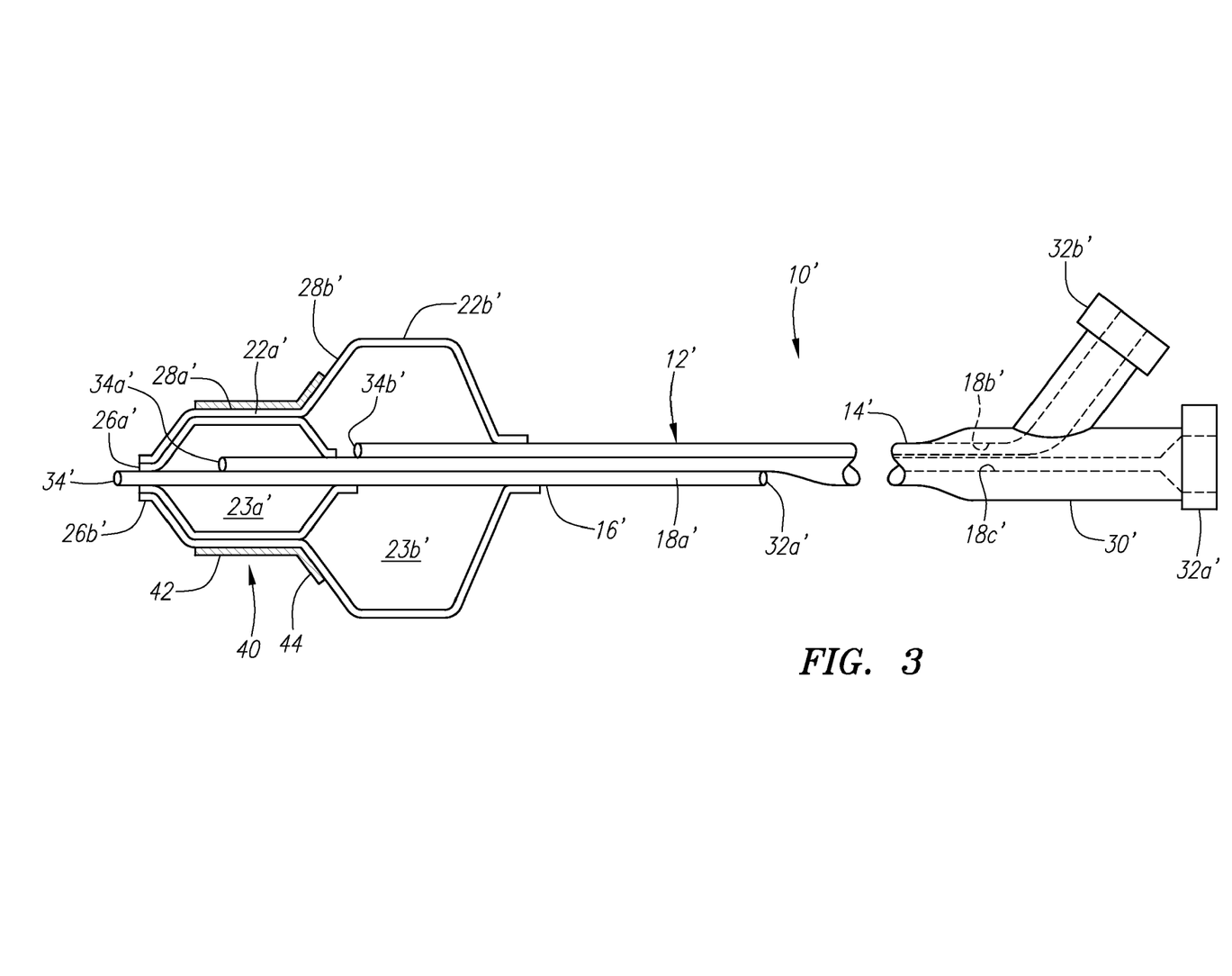
FIG. 3 is a partial cross-sectional side view of another embodiment of a balloon apparatus for delivering a stent into an ostium.

Turning to FIG. 3, in an alternative embodiment the apparatus 10' may include a catheter 12' including a plurality of tubular members disposed adjacent one another. The tubular members of the catheter 12' may be individual tubular bodies bonded or otherwise attached to one another along their lengths, a single body extruded or otherwise molded to include the tubular members as an integral unit, and the like. Otherwise, the materials and methods of the catheter 12' may be similar to the other embodiments described herein. Each tubular member may include a single or multiple lumens 18' therein. Optionally, different sections of the catheter 12' between the proximal end 14' and the distal end 16' may have different cross-sections. For example, the different sections along the length of the catheter 12' may be formed separately and attached to one another, e.g., by bonding, interference fit, melting or otherwise fusing the sections together, using an internal or external collar or sleeve (not shown), and the like. For example, as shown in FIG. 3, the distal end 14' includes three lumens 18,' while the proximal end 16' may include only two lumens 18b'- 18c.'

As shown in FIG. 3, the catheter 12' may include an instrument lumen 18a' that extends along the distal end 16' of the catheter 12' between a proximal opening 32a' and a distal opening 34a' in distal tip 17.' The proximal opening 32a' may be located a predetermined distance from the distal tip 17,' e.g., between about eighty to three hundred millimeters (80-300 mm), to provide a "rapid-exchange" apparatus that may facilitate quickly exchanging guidewires within the instrument lumen 18a.' Optionally, the proximal opening 32a' may include a ramped or tapered surface, e.g., to facilitate inserting and/or removing guidewires and the like into and out of the instrument lumen 18a.'

Returning to FIGS. 1 and 2 (although the materials and methods may be applicable to other embodiments described herein), the balloons 22 may be bonded or otherwise secured to the distal end 16 of the catheter 12. For example, ends 24, 26 of the balloons 22 may be attached to the distal end 16 by bonding with an adhesive, by sonic welding, using an annular collar or sleeve, and the like. The distal balloon 22a may include a proximal end 24a attached to the distal end 16 of the catheter 12 proximal to opening 34c and a distal end 26a attached adjacent the distal tip 17. The distal balloon 22a may be expandable from a contracted condition (not shown), which may facilitate advancement within a patient's vasculature, to an enlarged condition, as shown in FIGS. 1 and 2.

In the enlarged condition, the distal balloon 22a may include an intermediate portion 28a having a substantially uniform cross-section, as best seen in FIG. 2. Alternatively, the intermediate portion 28a may have other shapes if desired based upon anatomy encountered within a patient, e.g., a tapered shape that increases or decreases between the proximal and distal ends 24a, 26a. The intermediate portion 28a may have a length sufficient to receive at least a portion of a stent 40 thereon (as shown in FIG. 1), e.g., between about seven and thirty millimeters (7-30 mm). The distal balloon 22a may be tapered, blunt, or otherwise transition from the intermediate portion 28a to the proximal and distal ends 24a, 26a.

The proximal balloon 22b may include a proximal end 24b attached to the distal end 16 of the catheter 12 proximal to opening 34b and a distal end 26b attached to the distal balloon 22a, e.g., on or adjacent the intermediate portion 28a. The distal end 26b may be bonded with an adhesive, sonic welded, or otherwise attached to the distal balloon 22a to provide a substantially fluid-tight seam or bond. Thus, the balloons 22 may be expandable independent of one another, yet be inseparable from one another, e.g., to prevent any gaps or spaces from developing between the balloons 22. In one embodiment, the proximal balloon 22b may have a length that is substantially shorter than the distal balloon 22a, e.g., between about five to fifty millimeters (5-15 mm). In addition or alternatively, at least a transverse distal surface 28b of the proximal balloon 22b may have a length that is less than the length of the intermediate portion 28a of the distal balloon 22a.

In an alternative embodiment, as shown in FIG. 3, the proximal balloon 22b' may extend at least partially over the distal balloon 22a.' For example, the distal end 26b' of the proximal balloon 22b' may extend over the intermediate portion 28a' of the distal balloon 22a' and be attached over or adjacent to the distal end 26a' of the distal balloon 22a,' e.g., by bonding, sonic welding, and the like, as described elsewhere herein. This alternative may provide a seam that is substantially smaller, less bulky, more reliable, and/or easier to manufacture than the seam shown in FIG. 2.

Figure 7:
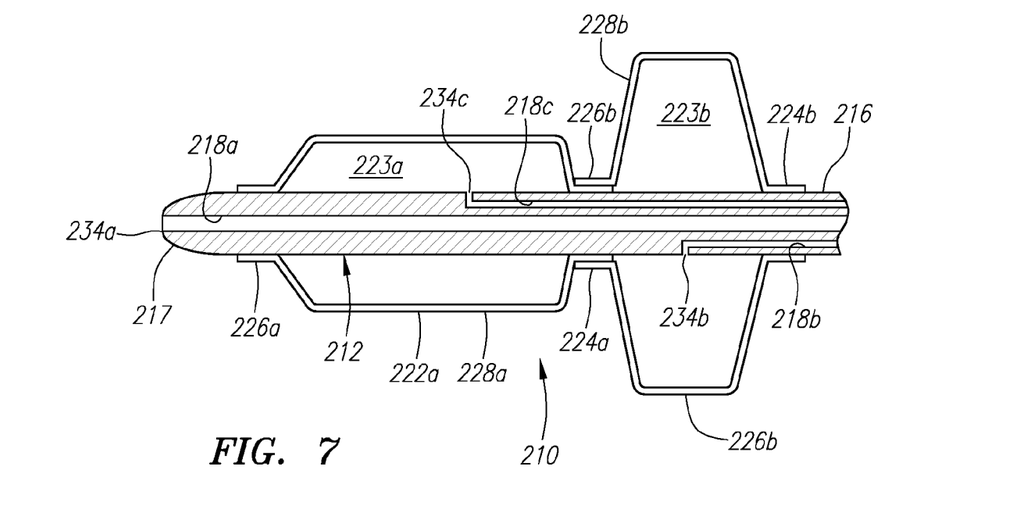
FIGS. 7 and 8 are cross-sectional side of a distal end of alternative embodiments of a balloon apparatus for delivering a stent into an ostium.

Turning to FIG. 7, in a further alternative, an apparatus 210 is shown having a catheter 212, including a distal end 216, and a pair of balloons 222a, 222b carried on the distal end 216, similar to the other embodiments described herein. Similar components have been identified with similar reference numbers (although increased by 100 or 200). Unlike previous embodiments, a distal end 226b of the proximal balloon 222b may be attached to the distal end 216 of the catheter 212 adjacent or directly to a proximal end 224a of the distal balloon 222a. For example, as shown, the distal end 226b of the proximal balloon 222b may be bonded or otherwise attached over the proximal end 224a of the distal balloon 222a. The proximal and distal ends 224a, 226a of the distal balloon 222a and the proximal end 224b of the proximal balloon 222b may be attached directly to the distal end 216 of the catheter 212, similar to the previous embodiments. Alternatively, the proximal end 224a of the distal balloon 222a may be attached over the distal end 226b of the proximal balloon 222b, which may be attached to the distal end 216 of the catheter 212 (not shown). This embodiment may introduce a small gap between the intermediate region 228*a* and the transverse surface 228*b* of the balloons 222 when they are expanded, as shown in FIG. 7.

Figure 8:
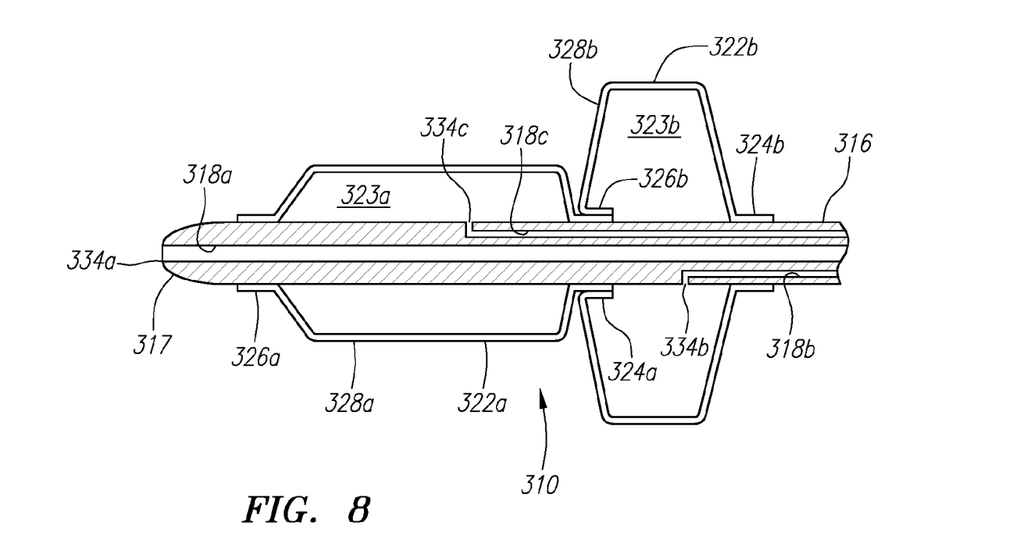

Alternatively, as shown in FIG. 8, the distal end 326*b* of the proximal balloon 322*b* may be everted partially into the interior 323*b* of the proximal balloon 322*b*, e.g., to minimize any gap between the balloons 322. For example, the proximal and distal ends 324*a*, 326*a* of the distal balloon 322*a* may be attached to the distal end 316 of the catheter. The distal end 326*b* of the proximal balloon 322*b* may be attached to the proximal end 324*a* of the distal balloon 322*a* such that the transverse surface 328*b* of the proximal balloon 322*b* is disposed immediately adjacent the intermediate region 328*a* of the distal balloon 322*a*.

Returning to FIG. 2, the proximal balloon 22*b* may be expandable from a contracted condition (not shown), which may facilitate advancement through a patient's vasculature to an enlarged condition. As shown, the proximal balloon 22*b* may be expandable independent of the distal balloon 22*a*. In the enlarged condition, the proximal balloon 22*b* may include a transverse distal surface 28*b* that extends transversely relative to the longitudinal axis 18 and/or intermediate portion 28*a* when the proximal balloon 22*b* is expanded. As shown in FIG. 2, the transverse surface 28*b* may define a substantially obtuse angle with the intermediate portion 28*a* of the distal balloon 22*a*, e.g., between about ninety and one hundred fifty degrees (90-150°).

Figure 4A:
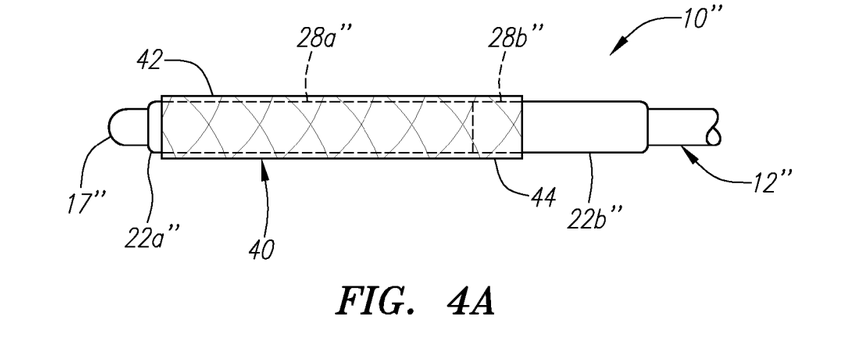
FIGS. 4A-4C are side views of a distal end of yet another embodiment of a balloon apparatus for delivering a stent into an ostium.
Figure 4B:
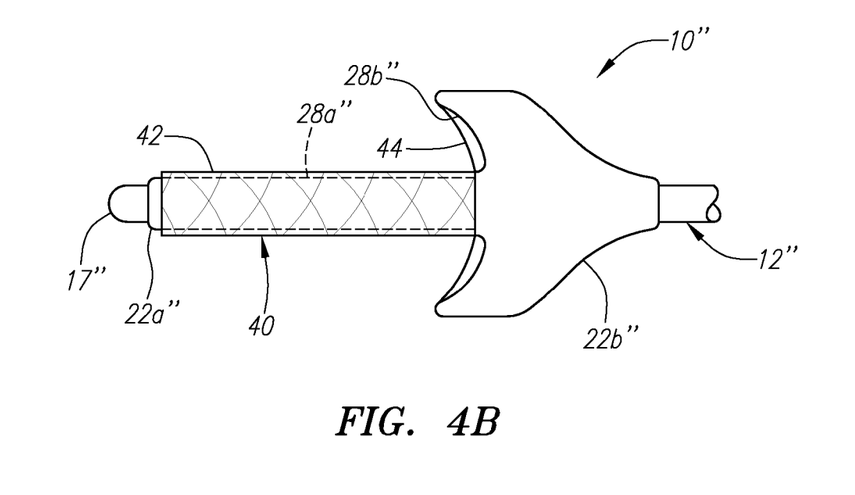
Figure 4C:
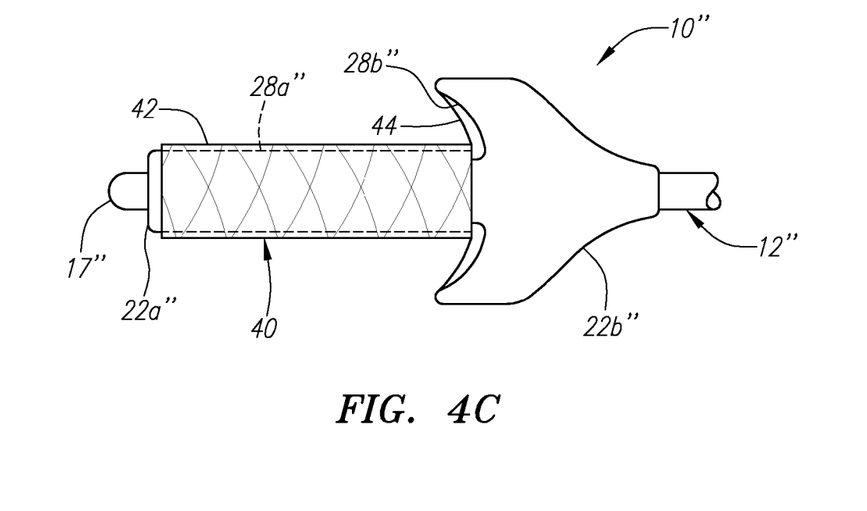

Alternatively, as shown in FIGS. 4B and 4C, the transverse surface 28*b*" may define a substantially acute angle with the intermediate portion 28*a*," e.g., between about sixty and ninety degrees (60-90°). In this alternative, the transverse surface 28*b*" may define a concave shape or space into which the distal balloon 22*a*" may at least partially nest as it expands, i.e., such that the distal balloon 22*a*" expands against the transverse surface 28*b*," as shown in FIG. 4C.

Returning to FIGS. 1 and 2, the balloons 22 may be formed from substantially inelastic material, e.g., PET, nylon, or PEBAX, such that the balloons 22 expand to a predetermined size in their enlarged conditions once sufficient fluid is introduced into the interiors 23 of the balloons 22. For example, the distal balloon 22*a* may be expandable to an enlarged condition in which the intermediate portion 28*a* has a diameter between about two to seven millimeters (2-7 mm), while the proximal balloon 22*b* may be expandable to a diameter between about four to twenty millimeters (4-20 mm). The distal balloon 22*a* may be expandable to an enlarged condition that is smaller than the proximal balloon 22*b*, e.g., such that the transverse surface 28*b* of the proximal balloon 22*b* extends radially outwardly from the intermediate portion 28*a* of the distal balloon 22*a* when both balloons 22 are expanded.

Alternatively, one or both of the balloons 22 may be formed from substantially elastic material, e.g., silicone, polyurethane, or polyethylene, such that the balloons 22 may be expanded to a variety of sizes depending upon the volume and/or pressure of fluid within the interiors 23. For example, in the embodiment shown in FIGS. 4A-4C, the distal balloon 22*a*" may be substantially elastic, while the proximal balloon 22*b*" is substantially inelastic. As shown, a stent 40 may be disposed over the balloons 22," e.g., such that a first portion 42 of the stent 40 overlies the distal balloon 22*a*" and a second portion 44 of the stent 40 overlies the proximal balloon 22*b*."

As shown, the proximal balloon 22*b*" may be expandable from a contracted condition (shown in FIG. 4A) to a predetermined size and shape in an enlarged condition (shown in FIGS. 4B and 4C). As the proximal balloon 22*b*" is expanded, the transverse surface 28*b*" bears against the second portion 44 of the stent 40, causing the second portion 44 to flare outwardly or otherwise deform, as shown in FIG. 4B. If the proximal balloon 22*b*" is substantially inelastic, the resulting flare of the second portion 44 may adopt a predetermined shape, e.g., a substantially straight or curved conical shape. The predetermined shape may be configured to correspond at least partially to a shape of an ostium within a patient's vasculature, as explained further below. Optionally, the proximal balloon 22*b*" may be at least somewhat compliant, e.g., such that, once fully inflated, the proximal balloon 22*b*" may be pressed against tissue surrounding the ostium with sufficient force to cause the proximal balloon 22*b*" to conform at least partially to the shape of the ostium. This action may cause the second portion 44 of the stent 40 to deform further, e.g., to conform to the shape of the ostium, which may enhance seating or securing the stent 40 at a target location, as explained further below.

Turning to FIG. 4C, the distal balloon 22*a*" may be substantially elastic or otherwise more compliant than the proximal balloon 22*b*." After expanding the proximal balloon 22*b*" to deform the second portion 44 of the stent 40 (as in FIG. 4B), the distal balloon 22*a*" may be expanded, e.g., to cause the first portion 42 of the stent 40 to expand radially outwardly. As the internal pressure within the distal balloon 22*a*" is increased (i.e., as additional fluid is delivered into the distal balloon 22*a*"), the distal balloon 22*a*" may be expanded through a range of sizes, causing the first portion 42 of the stent 40 to expand radially outwardly.

Because of its greater compliance and/or elasticity, the distal balloon 22*a*" may be expanded until a desired size is attained, e.g., sufficient to dilate a branch body lumen communicating with the ostium or other target location, as explained further below. Fluoroscopy or other external imaging may be used as the distal balloon 22*a*" is expanded, e.g., to monitor expansion of the first portion 42 of the stent 40, which may indicate the degree of dilation occurring within the target location. In addition, the distal balloon 22*a*" may conform at least partially to the surrounding anatomy, e.g., distributing pressure more evenly along the intermediate portion 28*a*" such that the first portion 42 of the stent conforms to the substantially uniform shape of the intermediate portion 28*a*" of the distal balloon 22*a*." Alternatively, the distal balloon 22*a*" may be expandable to a predetermined size. This alternative may involve selecting an apparatus 10" having a distal balloon 22*a*" with an expanded size corresponding to the desired dilated size of the target location.

With additional reference to FIGS. 4A-4C, the apparatus 10" (or any of the other embodiments described herein) may carry a stent 40, which may be formed from a variety of materials that may be plastically deformed to allow expansion of the stent 40. For example, the stent 40 may be formed from metal, such as stainless steel, tantalum, MP35N, Niobium, Nitinol, and L605, plastic, or composite materials. In particular, the materials of the stent 40 may be plastically deformed under the pressures experienced when the balloons 22" are expanded, e.g., such that the first and/or second portions 42, 44 of the stent 40 are deformed beyond their elastic limit. Thus, when the balloons 22" are subsequently collapsed, the stent 40 may maintain its expanded configuration (e.g., that shown in FIG. 4C) with minimal recoil, e.g., the stent 40 material may resist collapsing back towards its reduced configuration (e.g., that shown in FIG. 4A) if the tissue surrounding the body lumen attempts to constrict or otherwise return to its occluded shape.

Alternatively, at least a portion of the stent 40 may be self-expanding. For example, one or both of the first and second portions 42, 44 may be biased to expand at least partially outwardly yet may be constrained over the balloons 22 in a contracted condition to facilitate delivery. In this alternative, the stent 40 may be formed from Nitinol or other shape memory or superelastic materials.

Optionally, the resistance of the stent 40 to expansion may be varied along its length. This performance of the stent 40 may be based upon mechanical properties of the material, e.g., which may involve heat treating one or more portions of the stent 40 differently than other portions. In addition or alternatively, the structure of the stent 40 may be varied, e.g., by providing struts, fibers, or other components in different portions having different widths, thicknesses, geometry, and the like. In one embodiment, the material of the first portion 42 may require greater force to expand than the second portion 44. Thus, the second portion 44 may be more easily plastically deformed, which may allow the proximal balloon 22b" to be expanded using lower pressure than the distal balloon 22a."

The stent 40 may be a generally tubular structure, e.g., including openings in a tubular wall that facilitate expansion of the stent 40 and/or allow tissue ingrowth. For example, the stent may be an elongate tube that has slots or other openings formed in the tube wall, e.g., by laser cutting, mechanical cutting, chemical etching, machining, and the like. Alternatively, the stent 40 may be a braided or other structure, e.g., formed from one or wires or other filaments braided or otherwise wound in a desired manner. Additional possible stent structures may include helical coil wires or sheets. If desired, one or more portions of the stent 40 may include a membrane, film, or coating (not shown), e.g., to create a nonporous, partially porous, or porous surface between cells of the stent 40.

For example, the second portion 44 of the stent 40 may include a substantially elastic membrane, e.g., PTFE, ePTFE, silicone, polyurethane, or polyethylene, that may be embedded into, coated onto, sandwiched around, or otherwise carried by the stent 40. The membrane may be substantially elastic such that the membrane may expand when the second portion 44 is flared or otherwise expanded. Alternatively, the membrane may be folded or otherwise compressed such that the membrane may unfold or otherwise to accommodate expansion as the stent 40 is expanded. The membrane may be provided on an outer and/or inner surface of the second portion 44. A membrane on the inner surface may facilitate recrossing the stent 40 at a later time after implantation. For example, after the stent 40 is implanted within a patient, it may be desirable to advance a guidewire or other instrument through the ostium into the branch vessel, e.g., to perform another procedure. This may occur during the same surgical procedure, or some time after the patient has recovered, e.g., when the branch vessel, lesion, or main vessel need subsequent treatment. The membrane may prevent the tip of a guidewire or other instrument from catching or tangling in the struts, cells, wires, or other structures of the stent 40. Instead, the membrane may provide a substantially smooth, possibly lubricious surface that may guide a guidewire through the stent 40 into the branch vessel.

In addition or alternatively, a membrane on the stent 40 may carry therapeutic or other compounds or materials. For example, a membrane on an outer surface of the stent 40 may be pressed into contact with the plaque, damaged tissue, or other material of the lesion, allowing the compound to act to enhance healing or otherwise treat the lesion.

Optionally, the stent 40 may include one or more radiopaque or other markers (not shown), e.g., to facilitate monitoring the stent 40 during advancement, positioning, and/or expansion. For example, a band of radiopaque material, e.g., gold, platinum, iridium, tungsten, or their alloys, may be provided on each end of the stent 40 and/or adjacent the location where the first and second portions 42, 44 meet. In addition or alternatively, the apparatus 10 may include one or more radiopaque markers (not shown), e.g., at one or more predetermined locations on the distal end 16 of the catheter 12 and/or on one or both balloons 22. For example, a band of radiopaque material (not shown) may be provided on or under the ends of the intermediate portion 28a of the distal balloon 22a or the transverse surface 28b of the proximal balloon 22b, e.g., to facilitate positioning the apparatus 10.

In addition or alternatively, the stent 40 may carry one or more therapeutic or other compounds (not shown) that may enhance or otherwise facilitate treatment of a target location within a patient's body. For example, the stent 40 may carry compounds that prevent restenosis at the target location.

Turning to FIGS. 5A-5F, an exemplary method is shown for delivering a stent 40 into an ostium 90, e.g., using an apparatus 10, which may be any of the embodiments described herein, and not necessarily limited to the embodiment shown and described with reference to FIGS. 1 and 2. The ostium 90 may be an opening in a wall of a first or main body lumen 92 that communicates with a second or branch body lumen 94. In an exemplary embodiment, the main body lumen 92 may be the aortic root and the branch body lumen 94 may be a coronary artery. It will be appreciated that the apparatus and methods described herein may be applicable to a variety of bifurcations or branch body lumens that extend transversely, e.g., laterally or substantially perpendicular, from a main body lumen, e.g., within a patient's vasculature or other systems.

Figures 5A, 5B, 5C:
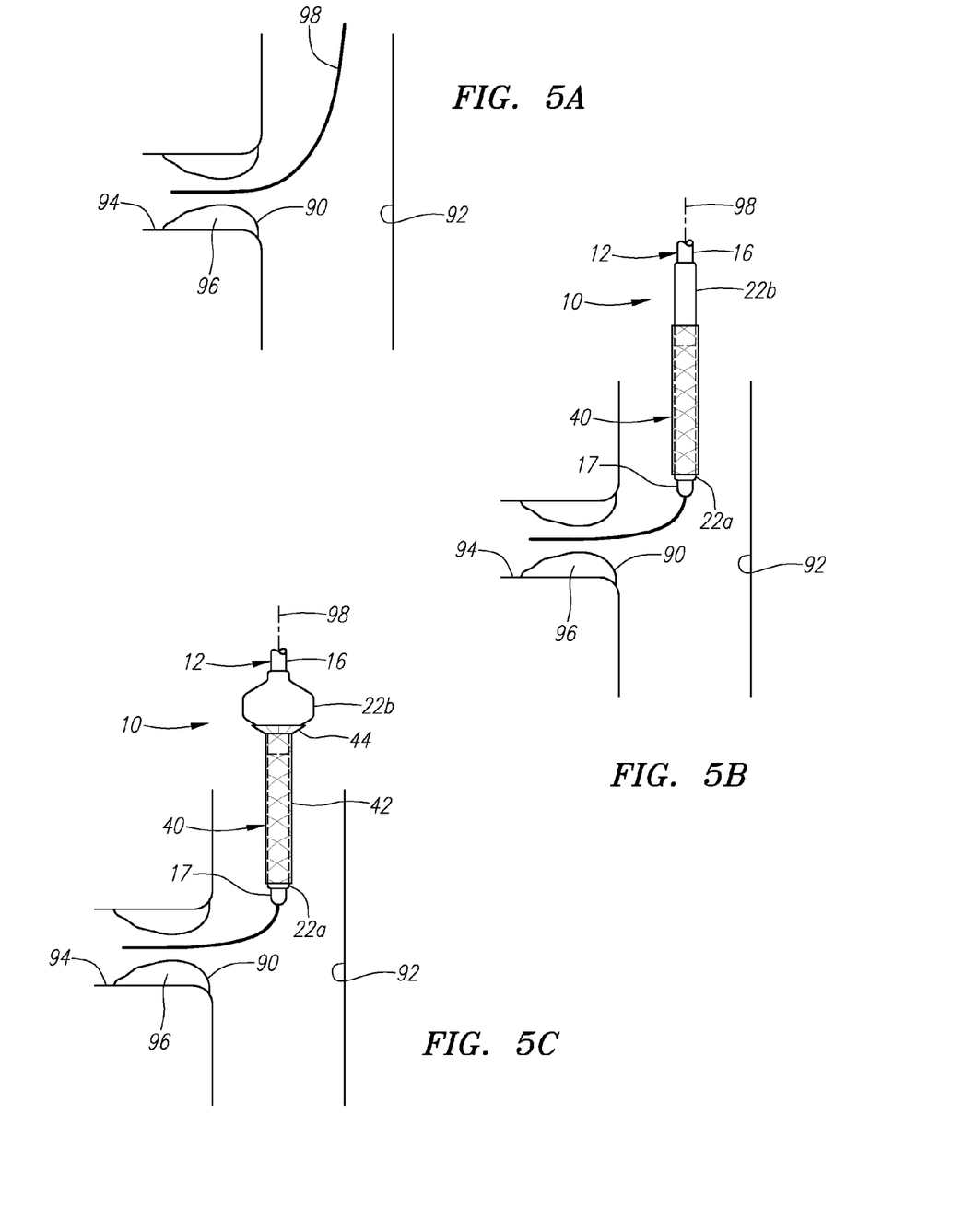
FIGS. 5A-5F are cross-sectional views of a patient's body, showing a method for implanting a stent within an ostium where a branch vessel extends from a main vessel.

An occlusion or other lesion 96 may exist at and/or adjacent to the ostium 90, e.g., extending at least partially into the branch 94. The lesion 96 may include atherosclerotic plaque or other material that partially or completely occludes blood or other fluid flow between the main body lumen 92 and the branch 94.

Initially, as shown in FIG. 5A, a guidewire 98 or other rail may be introduced from the main body lumen 92 through the ostium 90 into the branch 94. As shown, the lesion 96 at the ostium 90 partially occludes the ostium 90 and extends into the branch 94. The guidewire 98 may be placed using conventional methods. For example, a percutaneous puncture or cut-down may be created at a peripheral location (not shown), such as a femoral artery, carotid artery, or other entry site, and the guidewire 98 may be advanced through the patient's vasculature from the entry site, e.g., alone or with the aid of a guide catheter or sheath (not shown). If the lesion 96 completely occludes the branch 94, the guidewire 98 may be directed through the occlusion or other devices (not shown) may be advanced over the guidewire 98 or otherwise in conjunction with the guidewire 98 to create a passage through the lesion 96 for the guidewire 98.

After the guidewire 98 is directed into the branch 94 beyond the lesion 96, it may be desirable to at least partially dilate the lesion 96. For example, a balloon catheter (not shown) may be advanced over the guidewire 98 into and through the lesion 96, whereupon a balloon or other element on the catheter may be expanded to at least partially dilate the lesion 96. If desired, other procedures may also be performed at the lesion 96, e.g., to soften, remove, or otherwise treat plaque or other material forming the lesion 96, before the stent 40 is implanted. After completing any such procedures, instruments advanced over the guidewire 98 may be removed.

Optionally, a guide catheter (not shown) may be advanced over the guidewire 98 into the main body lumen 92, e.g., until a distal end of the guide catheter is disposed adjacent or proximal to the ostium 90. The guide catheter may be used to advance one or more instruments (such as those just described) over the guidewire 98 and into the main body lumen 92 and/or branch body lumen 94. In addition, the guide catheter may facilitate advancement of the apparatus 10 into the main body lumen 92 and/or into the branch 94, in addition to or instead of the guidewire 98.

Turning to FIG. 5B, a distal end 16 of apparatus 10 may be advanced over the guidewire 98 (and/or through the guide catheter, not shown) from the entry site into the main body lumen 92 with the balloons 22 in their contracted conditions. When the distal tip 17 is adjacent to the ostium 90, as shown in FIG. 5C, the proximal balloon 22b may be expanded, e.g., by delivering saline, nitrogen, or other inflation media into the interior 23b (see, e.g., FIG. 2) of the proximal balloon 22b from a syringe or other fluid source (not shown) coupled to the proximal end (also not shown) of the apparatus 10. As the proximal balloon 22b is expanded, a second portion 44 of the stent 40 is expanded, e.g., into a flared configuration conforming to the transverse surface 28b of the proximal balloon 22b.

Figure 5D:
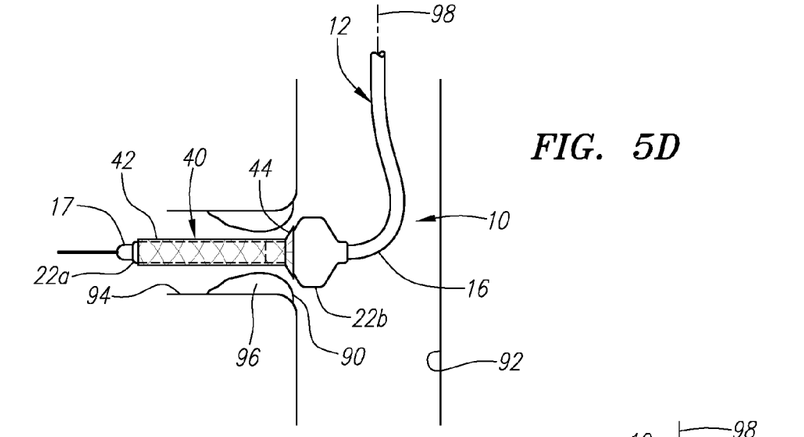

Turning to FIG. 5D, with the second portion 44 flared or otherwise expanded, the apparatus 10 may be advanced distally over the guidewire 98 into the ostium 90, e.g., until the second portion 44 contacts the wall of the main body lumen 92 surrounding the ostium 90. As the apparatus 10 is advanced, the distal tip 17 of the catheter 12 enters the ostium 90 and passes through the lesion 96 into the branch 94, e.g., until the first portion 42 of the stent 40 is disposed within the lesion 96, as shown. Optionally, if the stent 40 includes one or more radiopaque markers, fluoroscopy or other external imaging may be used to ensure that the stent 40 is positioned properly into the ostium 90 and branch 94.

Figure 5E:
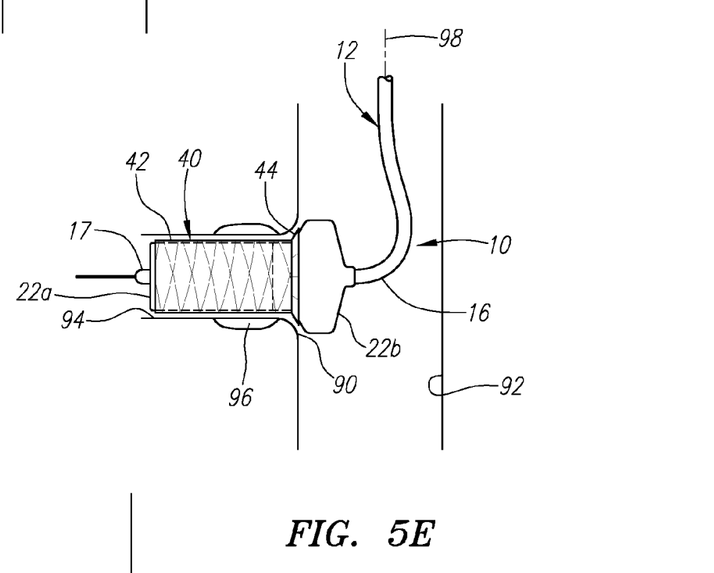

Turning to FIG. 5E, with the first portion 42 disposed within the lesion 96, the distal balloon 22a may be expanded, thereby dilating or otherwise lining the branch 94 within the lesion 96. For example, as the first portion 42 of the stent 40 is expanded, plaque and/or other material defining the lesion 96 may be directed radially outwardly to dilate the lesion 96 to a diameter comparable to the branch 94 downstream of the lesion 96. Again, if the stent 40 and/or apparatus 10 include one or more radiopaque markers or if contrast is delivered into the main body lumen 92 and/or into the branch 94, the ostium 90 and/or lesion 96 may be imaged to confirm the position of the stent 40 and/or to monitor the extent of dilation of the lesion 96, e.g., until a desired diameter or other cross-section is attained.

Optionally, additional distal force may be applied to the apparatus 10, e.g., to force the second portion 44 of the stent 40 against the ostium 90. This pushing may cause the second portion 44 to plastically deform further, e.g., to at least partially conform to the shape and/or contour of the ostium 90. This additional force may be applied before, during, or after inflation of the distal balloon 22a.

In addition or alternatively, if the proximal balloon 22b is elastically expandable, the proximal balloon 22b may be expanded initially (e.g., during the stage described with reference to FIGS. 5C and 5D) to a first enlarged configuration to allow the second portion 44 of the stent 40 to contact and/or otherwise seat into the ostium 90. Once the distal balloon 22a is inflated to expand the first portion 42 of the stent 40 and dilate the lesion 96 to a desired extent (e.g., as described with reference to FIG. 5E), the proximal balloon 22b may be inflated further, e.g., to further expand the second portion 44 of the stent 40 or cause the second portion 44 to conform further to the contour of the ostium 40. This additional expansion may further seat and/or secure the stent 40, and/or to dilate the ostium 90. Alternatively, the distal balloon 22a may be at least partially expanded before expanding the proximal balloon 22b.

Figure 5F:
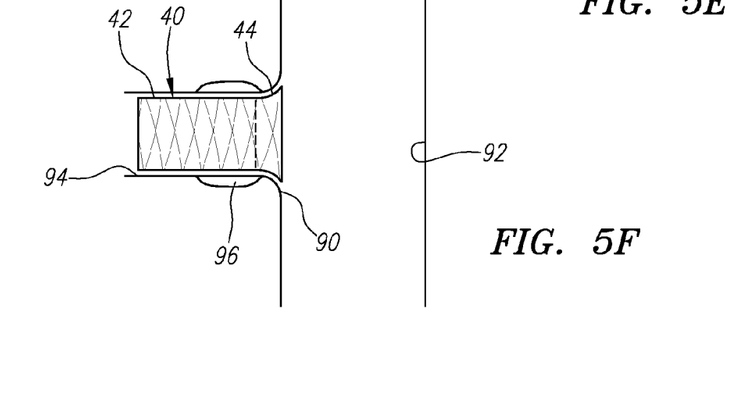

Turning to FIG. 5F, once the stent 40 is expanded and/or positioned in a desired manner, the balloons 22 may be collapsed, e.g., by evacuating the inflation media using a syringe or other device (not shown) at the proximal end (also not shown) of the catheter 12. The balloons 22 may be deflated simultaneously or sequentially, e.g., first deflating the distal balloon 22a, and then deflating the proximal balloon 22b (e.g., after applying further distal force, if desired). With the balloons 22 collapsed, the apparatus 10 is withdrawn from the main body lumen 92 and out of the patient's body. If a guide catheter or other sheath (not shown) is used, the guide catheter or sheath may be advanced against or into the ostium 90 before the apparatus 10 is removed, e.g., to facilitate withdrawing the balloons 22 without dislodging the stent 40. The guidewire 98 (and/or the guide catheter or sheath, if used) may be removed before, after, or simultaneously with the apparatus 10. Thus, the stent 40 remains in place to dilate the lesion 96.

Although the methods described include advancing the apparatus 10 into the branch 94 from the main body lumen 92, it will be appreciated that, in some procedures, the apparatus 10 may be advanced from the branch 94 into the main body lumen 92. In such procedures, the configuration of the balloons 22 may be reversed, i.e., the location of the proximal and distal balloons 22b, 22a may be reversed. In addition, in some embodiments, the apparatus 10 may include more than two balloons (not shown), which may be expanded independently of one another, e.g., to dilate, flare, or otherwise shape a stent during deployment in a desired manner. For example, a proximal balloon may be expanded first, and then individual balloons may be expanded sequentially, e.g., further distally along the distal end of the catheter, to expand the stent into a desired configuration within the ostium and/or branch.

The apparatus and method described herein may allow a lesion to be dilated even if the plaque or other material extends from the branch at least partially into the ostium and/or into the main body lumen. For example, the flared shape of the second portion 44 of the stent 40 shown in FIG. 5F may substantially reduce the risk of plaque extending inwardly around the stent 40 even after deployment. In contrast, a straight or unflared stent (not shown) may be deployed too far into the ostium, e.g., such that plaque within the lesion may remain exposed between the end of the stent and the main body lumen, which may at least partially occlude the ostium. Alternatively, a straight or unflared stent may be deployed such that it extends partially from the ostium into the main body lumen. This configuration may reduce the risk of at least partially occluding the ostium, but may make subsequently accessing the branch more difficult, e.g., if additional treatment is required at a later time.

Figure 6A:
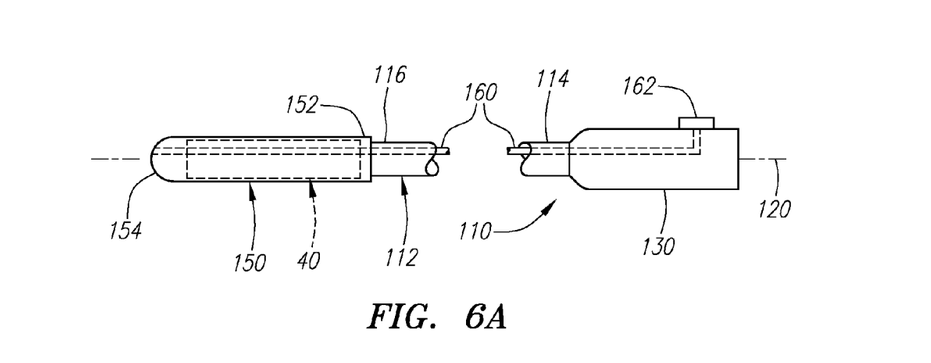
FIGS. 6A-6C are side views of a distal end of still another embodiment of a balloon apparatus including a movable sheath for covering and uncovering a stent carried on the apparatus.
Figure 6B:
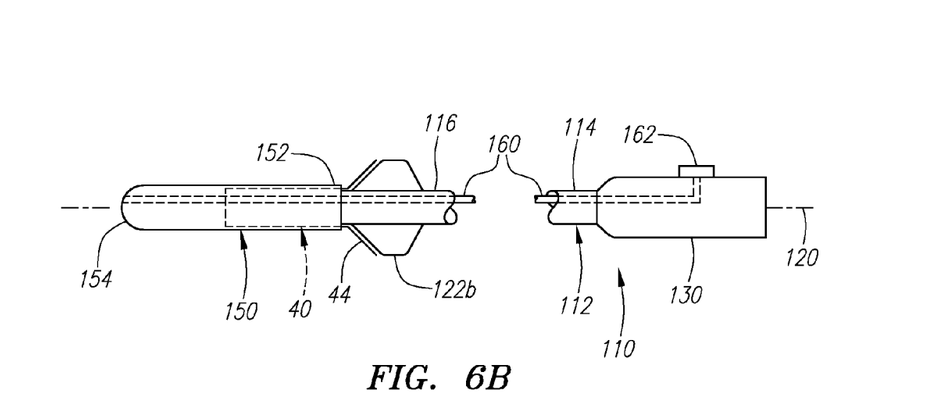
Figure 6C:
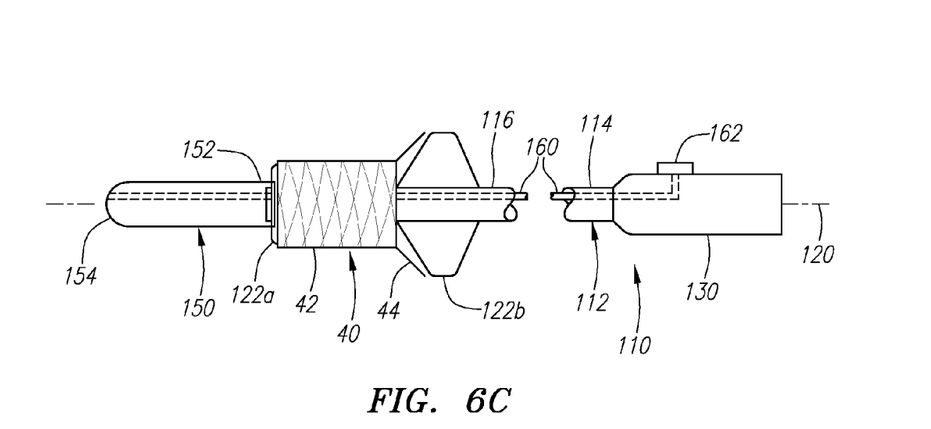

Turning to FIGS. 6A-6C, another embodiment of an apparatus 110 is shown that includes a catheter 112 including a proximal end 114, a distal end 116, and a plurality of lumens (not shown for clarity) extending therebetween, thereby defining a longitudinal axis 120. A pair of balloons 122 may be provided on the distal end 116, e.g., a distal balloon 122a and a proximal balloon 122b overlapping or otherwise adjacent the distal balloon 122a, similar to the other embodiments described herein. The catheter 112 may include one or more lumens (not shown), e.g., an instrument lumen and an inflation lumen for each balloon 122. A stent 40 or other prosthesis may be carried on the distal end 116, e.g., surrounding or otherwise over the balloons 122, also similar to the other embodiments described herein.

Unlike the previous embodiments, the apparatus 110 includes sheath 150 that at least partially covers the stent 40. For example, with the balloons 122 collapsed and the stent 40 in a contracted configuration, the sheath 150 may cover both a first or distal portion 42 and a second or proximal portion 44 of the stent 40, as shown in FIG. 6A. The sheath 150 may protect the stent 40 and/or balloons 122 during advancement of the apparatus 110, and/or may provide a rounded or otherwise substantially atraumatic tip for the apparatus 110, which may facilitate advancing the distal end 116 through a patient's vasculature.

As shown, the sheath 150 includes a proximal end 152 that covers the stent 40 and a distal end 154 that is disposed distal to the stent 40. The distal end 154 may have a tapered, rounded, or other shape, e.g., to provide a substantially atraumatic tip for the apparatus 110. A wire, cable, or other actuating element 160 may be coupled to the distal 154 and may extend proximally through or along the catheter 112 to the proximal end 114. For example, the catheter 112 may include an additional lumen and/or a groove or track (not shown) that accommodates the actuating element 160. The catheter 112 may include a handle 130 on the proximal end 114 including a slider or other control or actuator 162 coupled to the actuating element 160. As the actuator 162 is directed distally, the actuating element 160 may push the sheath 150 distally, e.g., to expose all or a portion of the stent 40.

In an exemplary embodiment, the actuator 162 may be directed from a proximal position (shown in FIG. 6A) to a first distal position, as shown in FIG. 6B, in which the first portion 42 of the stent 40 remains covered while the second portion 44 of the stent 40 is exposed. In this position, the proximal balloon 122b may be inflated, as shown, to flare or otherwise direct the second portion 42 of the stent 40 radially outwardly. Alternatively, if the second portion 44 of the stent 40 is self-expanding, the second portion 44 may automatically flare outwardly when the sheath 150 is directed to the first distal position. In this alternative, the proximal balloon 122b may be inflated to further flare or expand the second portion 44.

As shown in FIG. 6C, the actuator 162 may also be directed to a second distal position in which the first portion 42 of the stent 40 is exposed from the sheath 150. Once exposed, the distal balloon 122a may be inflated to expand the first portion 42 of the stent 40. Alternatively, the first portion 42 of the stent 40 may also be self-expanding such that the first portion 42 at least partially expands when the sheath 150 is directed to the second distal position. Thereafter, the distal balloon 122a may be inflated to further expand and/or shape the first portion 42 of the stent 40.

Alternatively, the sheath 150 may only cover the first portion 42 of the stent 40 (not shown). Optionally, an additional sheath, catheter, or other tubular member (not shown) may be provided that extends over the catheter 112 from the proximal end 114 to the distal end 116 and over at least the second portion 44 of the stent 40. If desired, this tubular member may mate with the proximal end 152 of the sheath 150 to provide a smooth or other desired transition. In yet another alternative, one or more other constraints may be provided over the stent 40, e.g., one or more filaments or other bindings (not shown) that may be wrapped around at least a portion of the stent 40. Such constraint(s) may be removed from the handle 130, e.g., by directing an actuator proximally to pull the bindings apart or otherwise from around the stent 40.

Returning to FIG. 6A, during use, the apparatus 110 may be provided initially with the balloons 122 collapsed and the stent 40 disposed over the balloons 122 in a contracted configuration, similar to the previous embodiments. The sheath 150 may extend over the first portion 42 and, optionally, over the second portion 44 of the stent 40, as shown in FIG. 6A. In this configuration, the apparatus 110 may be introduced into a patient's body and advanced into a main body lumen 92, similar to FIG. 5B. If the sheath 150 initially covers the second portion 42 of the stent 40, the sheath 150 may be directed distally to expose the second portion 42, as shown in FIG. 6B. Alternatively, if a separate tubular member covers the second portion 44, the tubular member may be retracted proximally to uncover the second portion 44.

Once exposed, the proximal balloon 122b may be inflated to flare or otherwise expand the second portion 42 of the stent 40, as shown in FIG. 6B, and similar to the procedure shown and described with reference to FIG. 5C. Similar to FIG. 5D, the apparatus 110 may be advanced to direct the sheath 150, and first portion 42 of the stent 40 covered thereby, into the ostium 90 and through a lesion 96 at least partially into the branch 94. Turning to FIG. 6C, the sheath 150 may then be directed distally to uncover the first portion 42 of the stent 40, whereupon the distal balloon 122a may be expanded, e.g., to dilate the lesion 96, similar to FIG. 5E. Additional inflation and/or manipulation of the balloons 122 and/or apparatus 110 may be completed, similar to the previous embodiments, e.g., to enhance seating the stent 40 and/or conforming the second portion 44 to the contour of the ostium 90. Once the stent is properly deployed, the balloons 122 may be collapsed, and the apparatus 110 may be removed, leaving the stent 40 to dilate the lesion 96.

It will be appreciated that elements or components shown with any embodiment herein are exemplary for the specific embodiment and may be used on or in combination with other embodiments disclosed herein. In addition, although balloons are described for expanding a stent, it will be appreciated that other expandable members may be provided on the apparatus described herein, e.g., instead of one or both of the proximal and distal balloons. For example, a pair (or more) mechanically expandable members may be provided on the distal end of a catheter that may be actuated from the proximal end of the catheter. A skin or other material may be provided that covers an expandable frame to cause the expandable members to expand to desired configurations, e.g., similar to the proximal and distal balloons described herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for implanting a prosthesis within an ostium extending from a main lumen into a branch lumen using an elongate member comprising first and second expandable members on a distal end of the elongate member, the prosthesis comprising first and second portions surrounding the first and second expandable members, respectively, the first portion having a length greater than the second portion and comprising material that requires greater force to expand than the second portion, the method comprising:

directing the distal end of the elongate member into the main lumen with the first and second portions in a contracted condition;

expanding the second expandable member to cause the second portion of the prosthesis to flare radially outwardly from the first portion within the main lumen while the first portion of the prosthesis remains in the contracted condition;

after expanding the second expandable member, directing the distal end into the branch lumen until the flared second portion contacts a wall of the main lumen surrounding the ostium and the first portion is disposed within the branch lumen;

after directing the distal end into the ostium, expanding the first expandable member to expand the first portion of the prosthesis to contact a wall of the branch lumen;

collapsing the first and second expandable members; and withdrawing the elongate member from the branch and main lumens, leaving the prosthesis with the first portion expanded within the branch lumen and the second portion contacting the wall of the main lumen surrounding the ostium.

2. The method of claim 1, wherein the first portion is expanded to dilate the branch lumen.

3. The method of claim 1, wherein the first portion is constrained while the second expandable member is expanded, and wherein the constraint is removed before expanding the first expandable member.

4. The method of claim 1, wherein the second portion is deformed as the second expandable member is expanded such that an acute angle is defined between the first and second portions.

5. The method of claim 1, wherein the second portion is deformed as the second expandable member is expanded such that an obtuse angle is defined between the first and second portions.

6. The method of claim 1, wherein the second portion is at least partially deformed as the distal end of the elongate member is directed into the branch lumen such that the second portion conforms at least partially to a shape of the wall of the main lumen surrounding the ostium.

7. The method of claim 1, wherein an internal pressure necessary to expand the second expandable member is less than an internal pressure necessary to expand the first expandable member.

8. The method of claim 1, wherein an internal pressure necessary to expand the first expandable member is less than an internal pressure necessary to expand the second expandable member.

9. The method of claim 1, further comprising expanding the second expandable member further after expanding the first expandable member.

10. The method of claim 9, wherein expanding the second expandable member further causes the second portion of the prosthesis to conform to the contour of the ostium.

11. The method of claim 9, wherein expanding the second expandable member further causes the prosthesis to dilate the ostium.

12. A method for implanting a prosthesis within an ostium extending from a main lumen into a branch lumen using an elongate member comprising first and second expandable members on a distal end of the elongate member, the prosthesis comprising first and second portions surrounding the first and second expandable members, respectively, the first portion having a length greater than the second portion and comprising material that requires greater force to expand than the second portion, the method comprising:

directing the distal end of the elongate member into the main lumen with the first and second portions in a contracted condition;

expanding the second expandable member to cause the second portion of the prosthesis to flare radially outwardly from the first portion within the main lumen while the first portion of the prosthesis remains in the contracted condition;

after expanding the second expandable member, directing the distal end into the ostium with sufficient force to cause the expanded second portion to engage a wall of the main lumen surrounding the ostium with the first portion disposed within the branch lumen;

after directing the distal end into the ostium, expanding the first expandable member to expand the first portion of the prosthesis to contact a wall of the branch lumen;

after expanding the first expandable member to expand the first portion of the prosthesis, expanding the second expandable member further to expand the second portion of the prosthesis further; and collapsing the first and second expandable members.

13. The method of claim 12, wherein the expanded second portion of the prosthesis is deformed to at least partially conform with the ostium when the distal end is directed into the ostium.

14. The method of claim 12, further comprising releasing at least a portion of the prosthesis such that the prosthesis at least partially expands resiliently before expanding at least one of the first and second expandable members to further expand the prosthesis.

15. The method of claim 12, wherein expanding the second expandable member further causes the second portion of the prosthesis to conform to the contour of the ostium.

16. The method of claim 12, wherein expanding the second expandable member further causes the prosthesis to dilate the ostium.

* * * * *